US00PP33259P2

(12) United States Plant Patent
Braeunig

(10) Patent No.: US PP33,259 P2
(45) Date of Patent: Jul. 13, 2021

(54) ***ACHILLEA* PLANT NAMED 'FLORACHYE0'**

(50) Latin Name: *Achillea millefolium*
Varietal Denomination: FLORACHYE0

(71) Applicant: Florensis B.V., Hendrik-Ido-Ambacht (NL)

(72) Inventor: Tobias M. Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 17/032,173

(22) Filed: Sep. 25, 2020

(51) Int. Cl.
*A01H 6/14* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Audrey Charles

(57) ABSTRACT

A new and distinct cultivar of *Achillea* plant named 'FLORACHYE0', characterized by its pale yellow-colored inflorescences, medium green-colored foliage, low growth vigor and compact, upright-mounded growth habit, is disclosed.

1 Drawing Sheet

Latin name of genus and species of plant claimed: *Achillea millefolium.*

Variety denomination: 'FLORACHYE0'.

BACKGROUND OF THE INVENTION

The present invention relates to a new and distinct cultivar of *Achillea* plant botanically known as *Achillea millefolium* and hereinafter referred to by the cultivar name 'FLORACHYE0'.

The new cultivar originated in a controlled breeding program in Quedlinburg, Germany during May 2011. The objective of the breeding program was the development of *Achillea* cultivars having attractive flower coloration and a compact growth habit suitable for container plantings.

The new *Achillea* cultivar is the result of open-pollination. The female (seed) parent of the new cultivar is the proprietary *Achillea millefolium* breeding selection coded 6177-4, not patented, characterized by its medium yellow-colored inflorescences, medium green-colored foliage, and vigorous, upright growth habit. The male (pollen) parent of the new cultivar is unknown. The new cultivar was selected as a single flowering plant within the progeny of the above stated open-pollination during July 2012 in a controlled environment in Quedlinburg, Germany.

Asexual reproduction of the new cultivar by terminal stem cuttings since July 2012 in Quedlinburg, Germany, Hendrik-Ido-Ambacht, The Netherlands, and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'FLORACHYE0' as a new and distinct cultivar of *Achillea* plant:

1. Pale yellow-colored inflorescences;

2. Medium green-colored foliage;
3. Low growth vigor; and
4. Compact, upright-mounded growth habit.

Plants of the new cultivar differ from plants of the female parent primarily in having a deeper yellow inflorescence color and a more compact growth habit.

Of the many commercially available *Achillea* cultivars, the most similar in comparison to the new cultivar is Milly Rock Red 'FLORACHRE1', U.S. Plant Pat. No. 31,757. However, in comparison, plants of the new cultivar differ from plants of 'FLORACHRE1' in at least the following characteristics:

1. Plants of the new cultivar have pale yellow-colored inflorescences unlike the dark red-colored inflorescences of plants of 'FLORACHRE1'; and
2. Plants of the new cultivar have disc florets that are a lighter shade of yellow than plants of 'FLORACHRE1'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'FLORACHYE0'. The plants were approximately five months old. The plants were transplanted from one-gallon containers and grown in a garden-type bed for 3 months in West Chicago, Ill. Plants were transplanted into a six-inch pot to photograph.

DETAILED BOTANICAL DESCRIPTION

Figure 1:
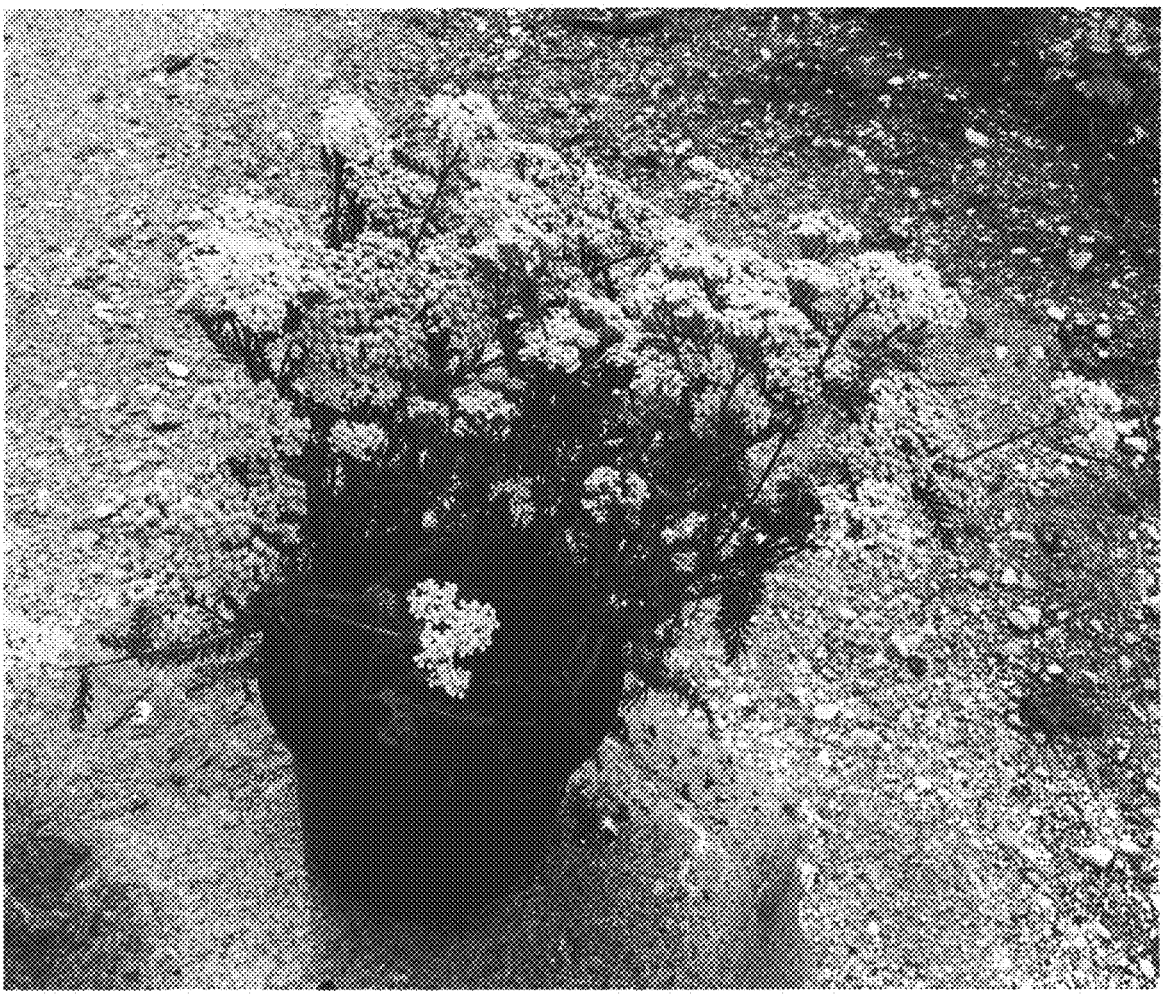
FIG. 1 illustrates a side view of the overall growth and flowering habit of 'FLORACHYE0'.
Figure 2:
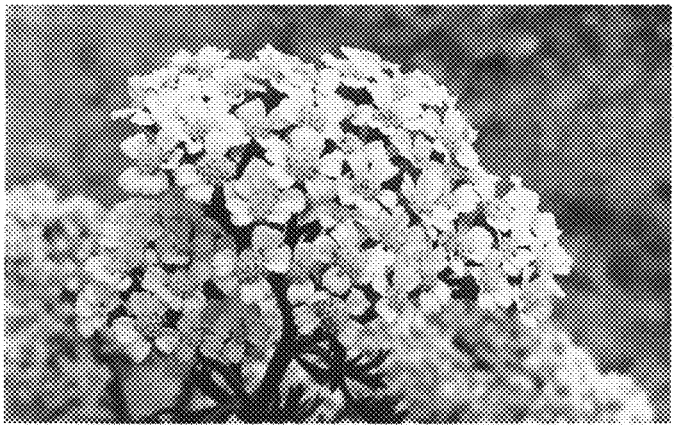
FIG. 2 illustrates a close-up view of an individual inflorescence of 'FLORACHYE0'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2020 under natural light conditions in Naperville, Ill.

The following descriptions and measurements describe approximately five-month old plants produced from cuttings from stock plants and grown under conditions comparable to those used in commercial practice. The plants were transplanted from one-gallon containers and grown outdoors in a garden-type bed for 3 months in West Chicago, Ill. Prior to transplant plants were grown in one-gallon containers for six weeks in a poly-covered greenhouse in Elburn, Ill. Greenhouse temperatures ranged from an average high of 60° F. (15.6° C.) to an average low of 45° F. (7.2° C.). No supplemental lighting was provided. Measurements and numerical values represent averages of typical plants.

Botanical classification: *Achillea millefolium* 'FLORACHYE0'.

Parentage:

*Female parent.*—Proprietary *Achillea millefolium* breeding selection coded 6177-4, not patented.

*Male parent.*—Unknown.

Propagation:

*Type cutting.*—Terminal stem.

*Time to initiate roots.*—Approximately 10 to 12 days.

*Time to produce a rooted cutting.*—Approximately 4 weeks.

*Root description.*—Thick fibrous.

*Rooting habit.*—Freely branching, moderately dense.

Plant description:

*Commercial crop time.*—Approximately 6 to 8 weeks from a rooted cutting to finish in a 15 cm pot.

*Growth habit and general appearance.*—Compact, upright-mounded.

*Hardiness.*—USDA Zone 5a (−20° F. to −15° F./ −28.9° C. to −26° C.).

*Size.*—Height from soil level to top of plant plane: Approximately 30.0 cm. Width: Approximately 36.0 cm.

*Branching habit.*—Freely branching, pinching enhances basal branching. Quantity of main branches per plant: Approximately 5.

*Branch.*—Strength: Strong. Length to base of cyme: Approximately 12.0 cm. Diameter: Approximately 3.0 mm. Length of central internode: Approximately 2.5 cm. Texture: Tomentose. Color of young stems: 146B. Color of mature stems: 146B.

Foliage description:

*General description.*—Quantity of leaves per main branch: Approximately 9. Fragrance: Faint. Form: Simple. Arrangement: Alternate.

*Leaves.*—Aspect: Acute angle to stem. Shape: Oblong. Margin: Very finely dissected giving a fern-like appearance. Apex: Acute. Base: Sessile, truncate. Venation pattern: Pinnate. Length of mature leaf: Approximately 8.5 cm. Width of mature leaf: Approximately 1.3 cm. Texture of upper surface: Sparsely pubescent. Texture of lower surface: Moderately pubescent. Color of upper surface of young and mature foliage: 137A with midvein of 147B. Color of lower surface of young and mature foliage: 138A with midvein of 147C.

Flowering description:

*Flowering habit.*—'FLORACHYE0' is freely flowering under outdoor growing conditions with substantially continuous blooming from late spring through summer.

*Lastingness of individual inflorescence on the plant.*—Approximately 10 to 14 days.

Inflorescence description:

*General description.*—Type: Rotate composite inflorescence form; inflorescences arranged in terminal or axillary compound cymes; cymes somewhat flat-topped; freely flowering; persistent. Aspect: Upward and outward. Quantity per plant: Approximately 12. Cyme diameter: Approximately 15.0 cm. Cyme depth: Approximately 9.0 cm. Inflorescence diameter: Approximately 7.0 mm. Inflorescence depth: Approximately 7.0 mm. Fragrance: Slight.

*Peduncle.*—Strength: Strong. Aspect: Erect. Length: Approximately 2.5 cm. Diameter: Approximately 3.0 mm. Texture: Tomentose. Color: 146B.

*Bud.*—Rate of opening: Generally takes 3 to 4 days for bud to progress from first color to fully open flower.

*Bud just before opening.*—Shape: Ovoid. Length: Approximately 5.0 mm. Diameter: Approximately 2.0 mm. Color: 146D and petals of 155D.

*Ray florets.*—Quantity per inflorescence: Approximately 4 to 5. Arrangement: In a single whorl. Aspect: Rotate. Shape: Orbicular on a narrow tube enclosing pistil. Margin: Entire. Apex: Three rounded tips. Base: Attenuate. Length: Blade portion approximately 2.0 mm to 3.0 mm, tube portion approximately 3.0 mm. Width: Blade portion approximately 2.0 mm to 3.0 mm, tube portion approximately 0.5 mm. Texture of upper and lower surfaces: Glabrous. Color of upper surface when first open: 2C with an overlay of 61A that is heaviest at margins. Color of lower surface when first and fully open: 158D. Color of upper surface when fully open: 2D. Color of tube portion: 145B.

*Disc florets.*—Quantity per inflorescence: Approximately 16. Arrangement: Massed in center of inflorescence. Shape: Tubular. Margin: Entire. Apex: Five-acute tips. Base: Fused. Length: Approximately 5.0 mm. Diameter at apex: Approximately 1.0 mm. Diameter at base: Approximately 1.0 mm. Texture: Sparsely glandular pubescent. Color when first and fully open: Tips of 2D, center of 145B, and base of 155D.

*Disc.*—Diameter: Approximately 3.0 mm. Depth: Approximately 1.5 mm.

*Receptacle.*—Shape: Dome. Height: Approximately 1.0 mm. Diameter at base: Approximately 2.5 mm. Color: 146D.

*Phyllaries.*—Quantity per inflorescence Approximately 14. Arrangement: In multiple whorls. Shape: Lanceolate to narrowly elliptic. Margin: Entire with papery edges. Apex: Acute. Base: Truncate. Length: Approximately 2.0 mm to 4.0 mm. Width: Approximately 1.0 mm to 1.5 mm. Texture of upper surface: Glabrous. Texture of lower surface: Sparsely pubescent. Color of upper surface: 146B. Color of lower surface: 146C.

*Reproductive organs.*—Androecium: Present on disc florets only. Stamen quantity: 5. Stamen length: Approximately 2.0 mm. Anther shape: Oblong. Anther length: Approximately 1.0 mm. Anther color: N199D. Pollen amount: Sparse. Pollen color: 23B. Gynoecium: Present on ray and disc florets. Pistil quantity: 1 per floret. Pistil length: Approximately 5.0 mm. Stigma shape: Bifid. Stigma length: Less than 1.0 mm. Stigma color: 2B. Style length: Approximately 3.0 mm. Style color: 145D. Ovary length: Approximately 2.0 mm. Ovary color: 155D.

Seed and fruit production: Neither seed nor fruit production has been observed.

Disease and pest resistance: Resistance to pathogens and pests common to *Achillea* has not been observed.

What is claimed is:

1. A new and distinct cultivar of *Achillea* plant named 'FLORACHYE0', substantially as herein illustrated and described.

* * * * *